US007907168B2

(12) United States Patent
Eino

(10) Patent No.: US 7,907,168 B2
(45) Date of Patent: Mar. 15, 2011

(54) ENDOSCOPE SYSTEM

(75) Inventor: Teruo Eino, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 2109 days.

(21) Appl. No.: 10/150,945

(22) Filed: May 21, 2002

(65) Prior Publication Data

US 2002/0175992 A1    Nov. 28, 2002

(30) Foreign Application Priority Data

May 22, 2001    (JP) ................................. 2001-152916

(51) Int. Cl.
*H04N 7/18* (2006.01)
(52) U.S. Cl. ........................................................ 348/65
(58) Field of Classification Search .............. 348/42–96, 348/98; 600/117, 118, 146, 109, 1; 707/104.1; 604/6.13; 375/240.15
See application file for complete search history.

(56) References Cited

U.S. PATENT DOCUMENTS

| | | | |
|---|---|---|---|
| 4,621,618 A | 11/1986 | Omagari | |
| 4,739,521 A | 4/1988 | Akimoto | |
| 5,217,003 A | 6/1993 | Wilk | |
| 5,249,121 A * | 9/1993 | Baum et al. ........................ 606/1 |
| 5,482,029 A * | 1/1996 | Sekiguchi et al. ............ 600/109 |
| 5,609,560 A | 3/1997 | Ichikawa et al. | |
| 5,622,528 A | 4/1997 | Hamano et al. | |
| 5,701,904 A | 12/1997 | Simmons et al. | |
| 5,894,322 A | 4/1999 | Hamano et al. | |
| 5,896,166 A * | 4/1999 | D'Alfonso et al. ............. 348/72 |
| 6,003,808 A | 12/1999 | Nguyen et al. | |
| 6,006,191 A | 12/1999 | DiRienzo | |
| 6,006,755 A | 12/1999 | Edwards | |
| 6,086,544 A * | 7/2000 | Hibner et al. .................. 600/568 |
| 6,120,435 A * | 9/2000 | Eino .............................. 600/118 |
| 6,223,100 B1 | 4/2001 | Green | |
| 6,224,542 B1 * | 5/2001 | Chang et al. .................. 600/109 |
| 6,259,806 B1 | 7/2001 | Green | |
| 6,295,082 B1 * | 9/2001 | Dowdy et al. ................... 348/72 |
| 6,393,431 B1 * | 5/2002 | Salvati et al. .............. 707/104.1 |
| 6,396,941 B1 | 5/2002 | Bacus et al. | |
| 6,413,233 B1 * | 7/2002 | Sites et al. ................... 604/6.13 |
| 6,428,470 B1 | 8/2002 | Thompson | |
| 6,436,032 B1 * | 8/2002 | Eto et al. ....................... 600/117 |
| 6,442,417 B1 | 8/2002 | Shahidi et al. | |
| 6,490,490 B1 | 12/2002 | Uchikubo et al. | |
| 6,569,086 B2 * | 5/2003 | Motoki et al. ................. 600/146 |

(Continued)

FOREIGN PATENT DOCUMENTS

JP    6-14867    1/1994

(Continued)

*Primary Examiner* — Tung Vo
(74) *Attorney, Agent, or Firm* — Dickstein Shapiro LLP

(57) ABSTRACT

An endoscope system is provided with an endoscope and an image display section that displays the image of a subject captured by an image pick-up element provided in this endoscope. The endoscope is provided with a connector whereby a serial communication cable is detachably connected and a signal processing circuit that converts the image captured by the image pick-up element to a signal capable of being transmitted through the serial communication cable. The image display section is a screen displayed on a display device of a terminal device connected to the serial communication cable; and the screen is provided with an image display region used for display of an image captured by the image pick-up element and a display region for control purposes whereby control of the endoscope is performed.

20 Claims, 6 Drawing Sheets

U.S. PATENT DOCUMENTS

| | | |
|---|---|---|
| 6,574,355 B2 | 6/2003 | Green |
| 6,581,117 B1 | 6/2003 | Klein et al. |
| 6,652,451 B2 * | 11/2003 | Murata et al. .................. 600/118 |
| 6,657,884 B2 | 12/2003 | Bocian et al. |
| 6,659,939 B2 | 12/2003 | Moll et al. |
| 6,681,061 B2 | 1/2004 | Agata et al. |
| 6,697,764 B2 | 2/2004 | Corby et al. |
| 6,791,601 B1 * | 9/2004 | Chang et al. ..................... 348/65 |
| 2001/0012023 A1 | 8/2001 | Kobayashi et al. |
| 2001/0047213 A1 | 11/2001 | Sepe, Jr. |
| 2001/0051762 A1 | 12/2001 | Murata et al. |
| 2002/0016718 A1 | 2/2002 | Rothschild et al. |
| 2002/0026096 A1 | 2/2002 | Motoki et al. |
| 2002/0032365 A1 | 3/2002 | Hasegawa et al. |
| 2002/0044049 A1 | 4/2002 | Saito et al. |
| 2002/0087048 A1 | 7/2002 | Brock et al. |
| 2002/0087049 A1 | 7/2002 | Brock et al. |
| 2003/0004397 A1 | 1/2003 | Kameya et al. |
| 2003/0050733 A1 | 3/2003 | Wang et al. |
| 2003/0053433 A1 | 3/2003 | Chun |
| 2003/0228039 A1 | 12/2003 | Green |
| 2004/0131282 A1 | 7/2004 | Yoshida et al. |
| 2004/0151358 A1 | 8/2004 | Yanagita et al. |

FOREIGN PATENT DOCUMENTS

| | | |
|---|---|---|
| JP | 11-211997 | 8/1999 |
| JP | 2000-245694 A | 9/2000 |

* cited by examiner

ENDOSCOPE SYSTEM

This application claims benefit of Japanese application No. 2001-152916 filed on May 22, 2001, the contents of which are incorporated by this reference.

BACKGROUND OF THE INVENTION

1. Field of the Invention

The present invention relates to an endoscope system whereby endoscopic examination is performed using an endoscope.

2. Description of the Related Art

U.S. Pat. No. 4,621,618 discloses an endoscope device arranged such that control can be performed using a centralized control device wherein a monitor, joystick and control buttons of various types are arranged in centralized fashion and arranged such that the endoscope can be easily controlled at a location remote from the main endoscope unit while viewing the monitor screen.

Also, in a fourth embodiment disclosed in Laid-open Japanese Patent publication No. 11-211997 there is disclosed an endoscope image observation device constituted by combining a control box and a personal computer.

However, the endoscope device of U.S. Pat. No. 4,621,618 is of very high cost, since the centralized control device is a special-purpose device used for its purpose. Furthermore it is of large size and considerable weight owing to the provision of a joystick and a large number of control buttons. It is therefore very inconvenient to move the centralized control device to a desired location where examination is to be performed.

Furthermore, although in recent years it has become common to save observation images obtained from an endoscope on a computer, with such an endoscope, a computer for this purpose must be separately provided and an operation of transferring the image data from the endoscope to the computer must be performed.

On the other hand, while the fourth embodiment of Laid-open Japanese Patent publication No. 11-211997 solves some of the above problems, it is of very high cost, since the control box is a special-purpose device used for its purpose.

SUMMARY OF THE INVENTION

In view of the above, an object of the present invention is to provide an endoscope system whereby display of a captured image can be achieved at low cost and wherein control such as curvature control can be achieved.

A further object is to provide an endoscope system wherein endoscopic examination can be performed with the location of examination changed and wherein substitution can easily be performed in cases where for example the control device used for control etc. of the endoscope has broken down.

An endoscope system according to the present invention comprises an endoscope and an image display section that displays the image of a subject that is captured by an image pick-up element provided in the endoscope. The endoscope comprises a connector that is detachably connected to a serial communication cable and a signal processing circuit that converts the image captured by the image pick-up element to a signal capable of being transferred via the serial communication cable. The image display section is a screen displayed on a display device of a terminal device connected to the serial communication cable; the screen comprises an image display region utilized for display of the image captured by the image pick-up element and a display region for control purposes whereby control of the endoscope is performed.

The above and other objects, features and advantages of the invention will become more clearly understood from the following description referring to the accompanying drawings.

DESCRIPTION OF THE PREFERRED EMBODIMENTS

An embodiment of the present invention is described below with reference to the drawings.

Figure 1:
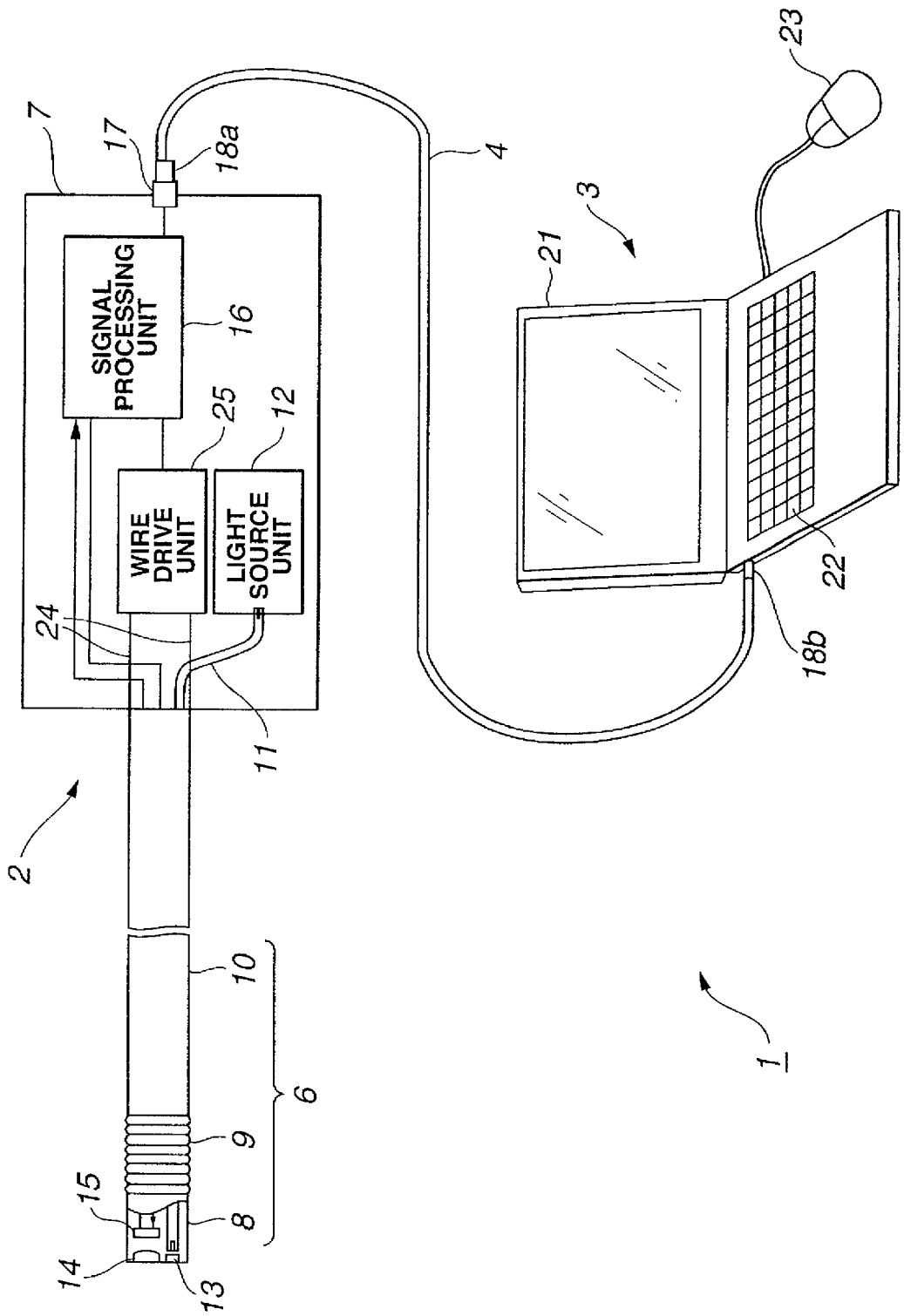
FIG. 1 is a view showing the overall configuration of an endoscope system according to an embodiment of the present invention.
Figure 2:
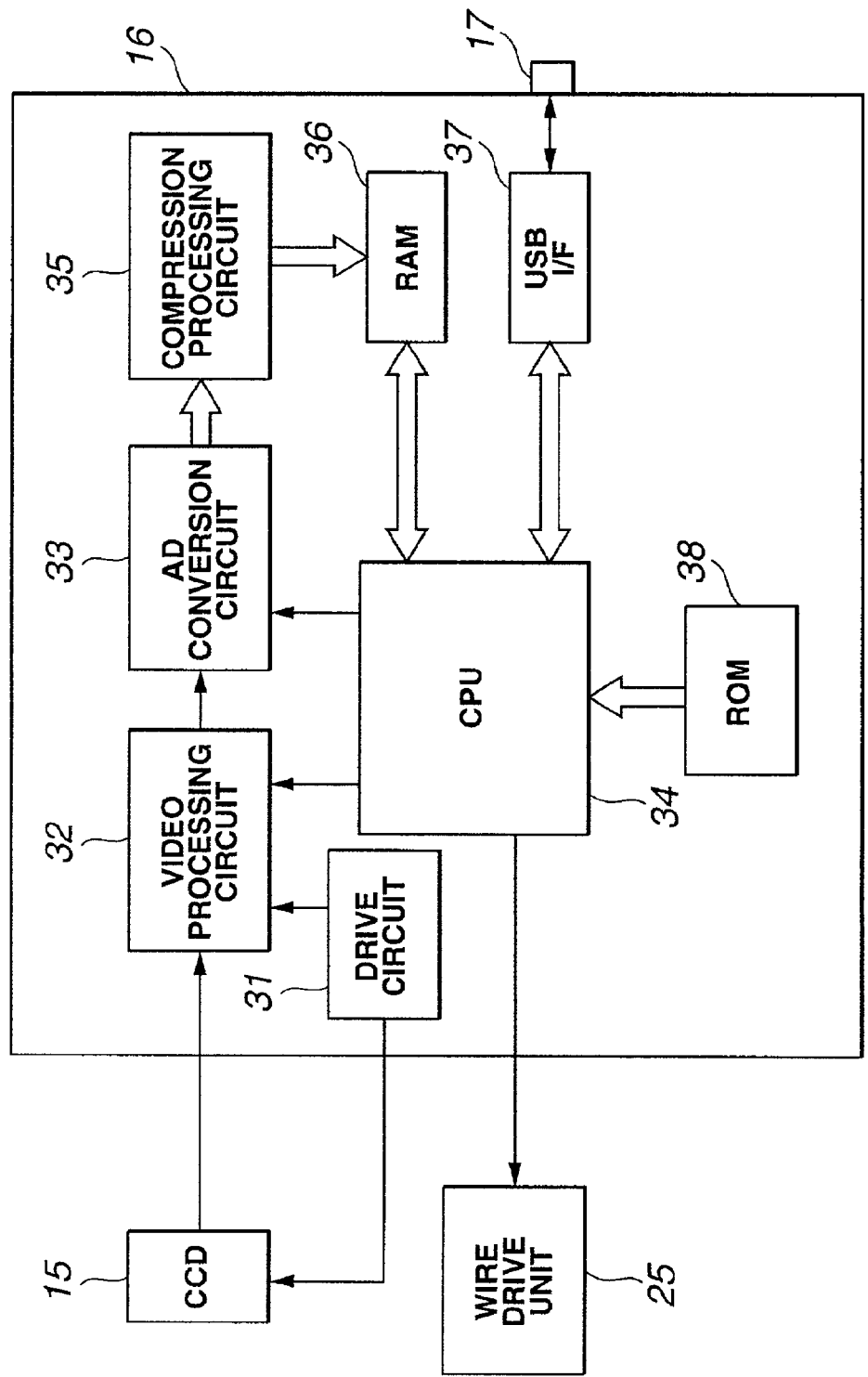
FIG. 2 is a block diagram illustrating the internal configuration of a signal processing unit according to the embodiment of the present invention.
Figure 3:
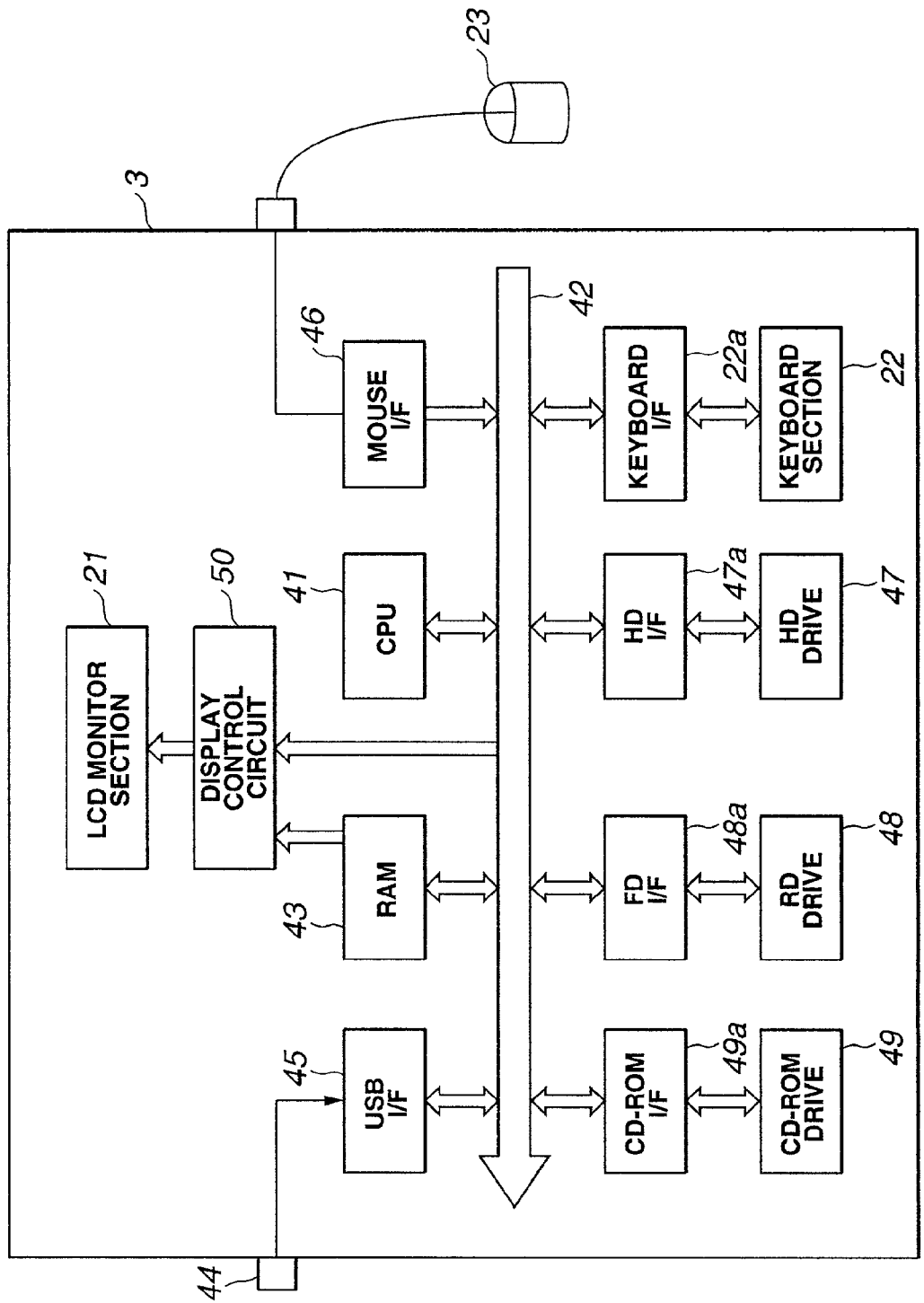
FIG. 3 is a block diagram illustrating the configuration of a personal computer according to the embodiment of the present invention.
Figure 4:
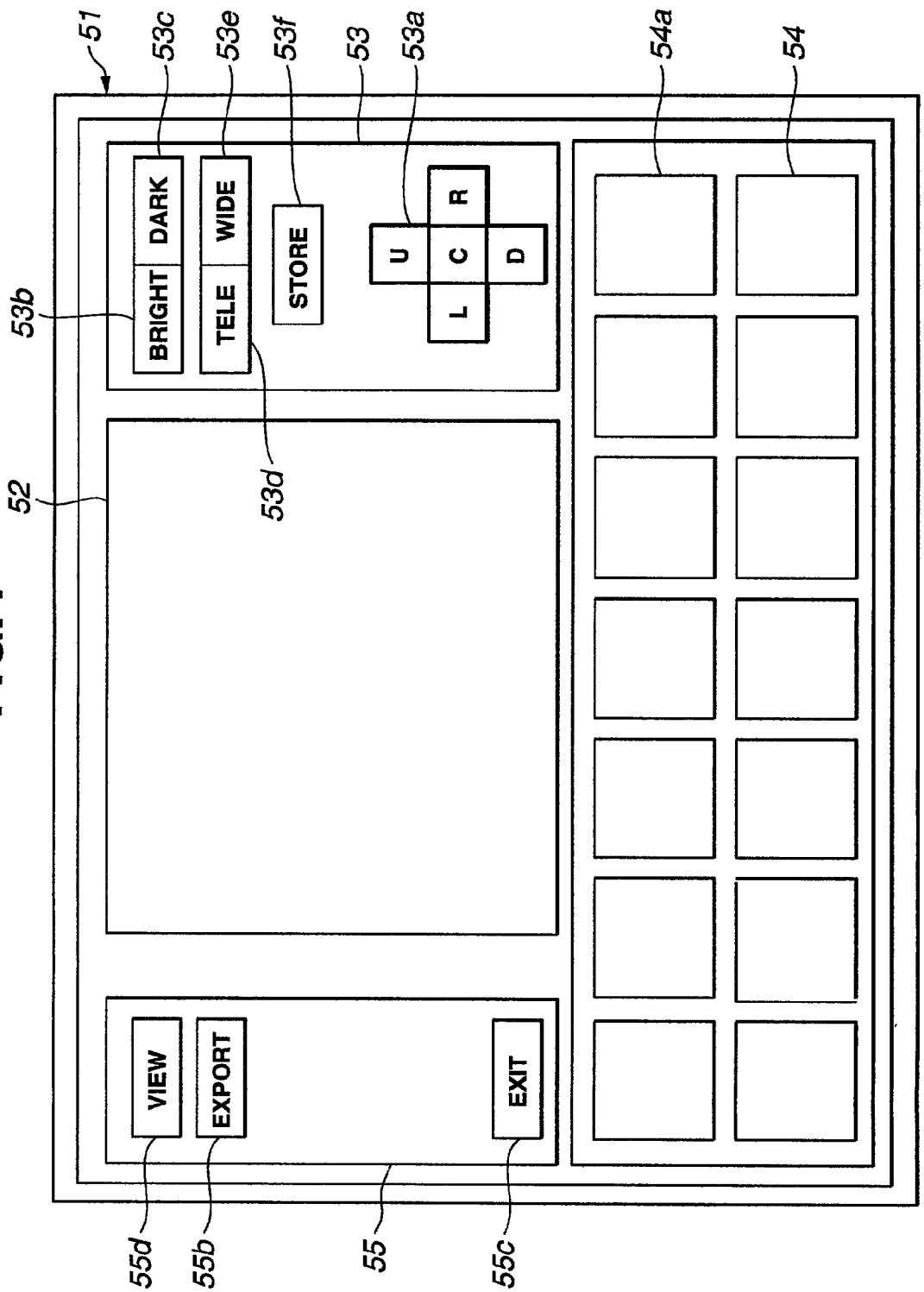
FIG. 4 is a view illustrating an example of the configuration of a display screen on an LCD monitor of a personal computer according to the embodiment of the present invention.
Figure 5:
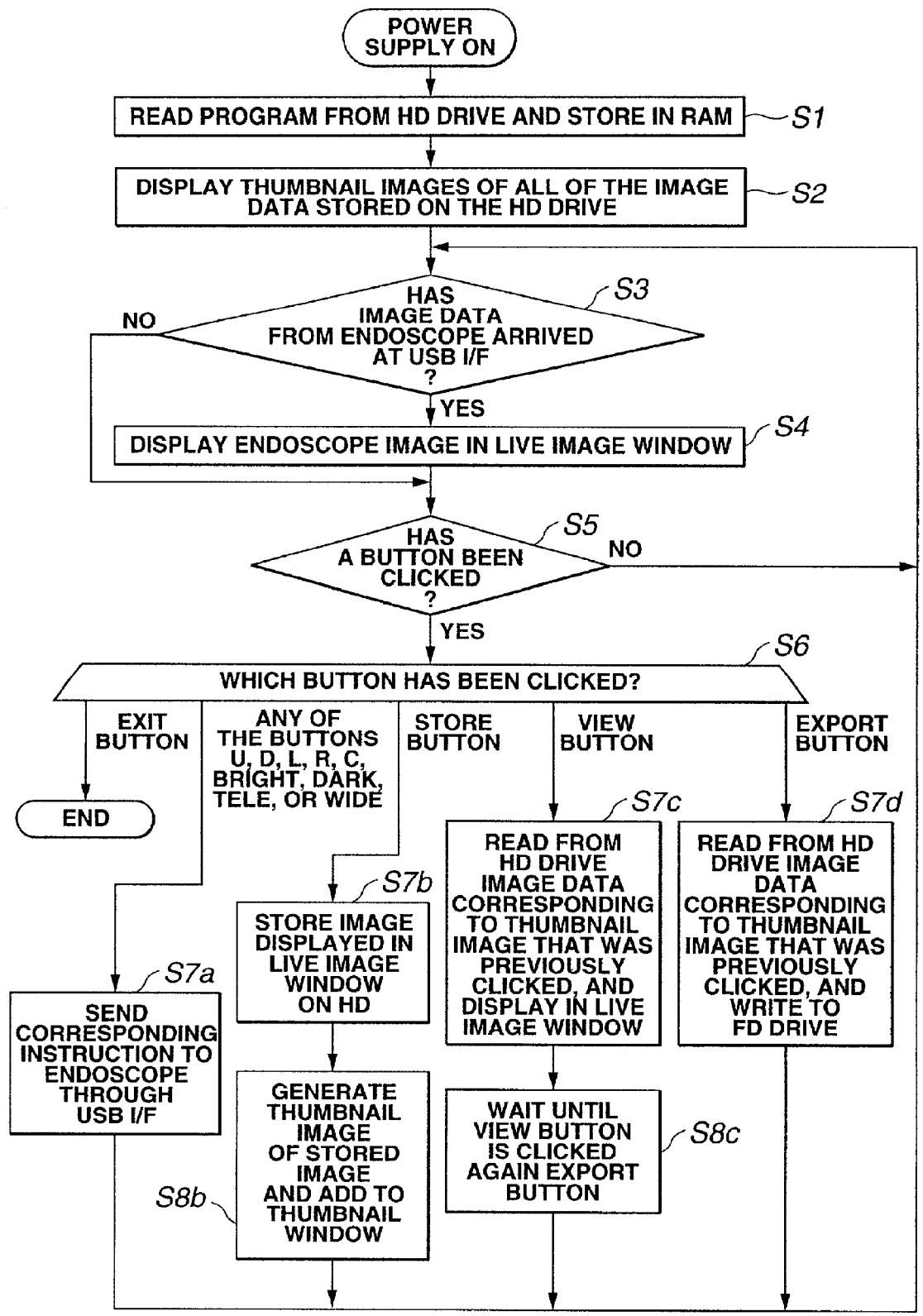
FIG. 5 is a flow chart illustrating the content of processing of a personal computer according to the embodiment of the present invention.
Figure 6:
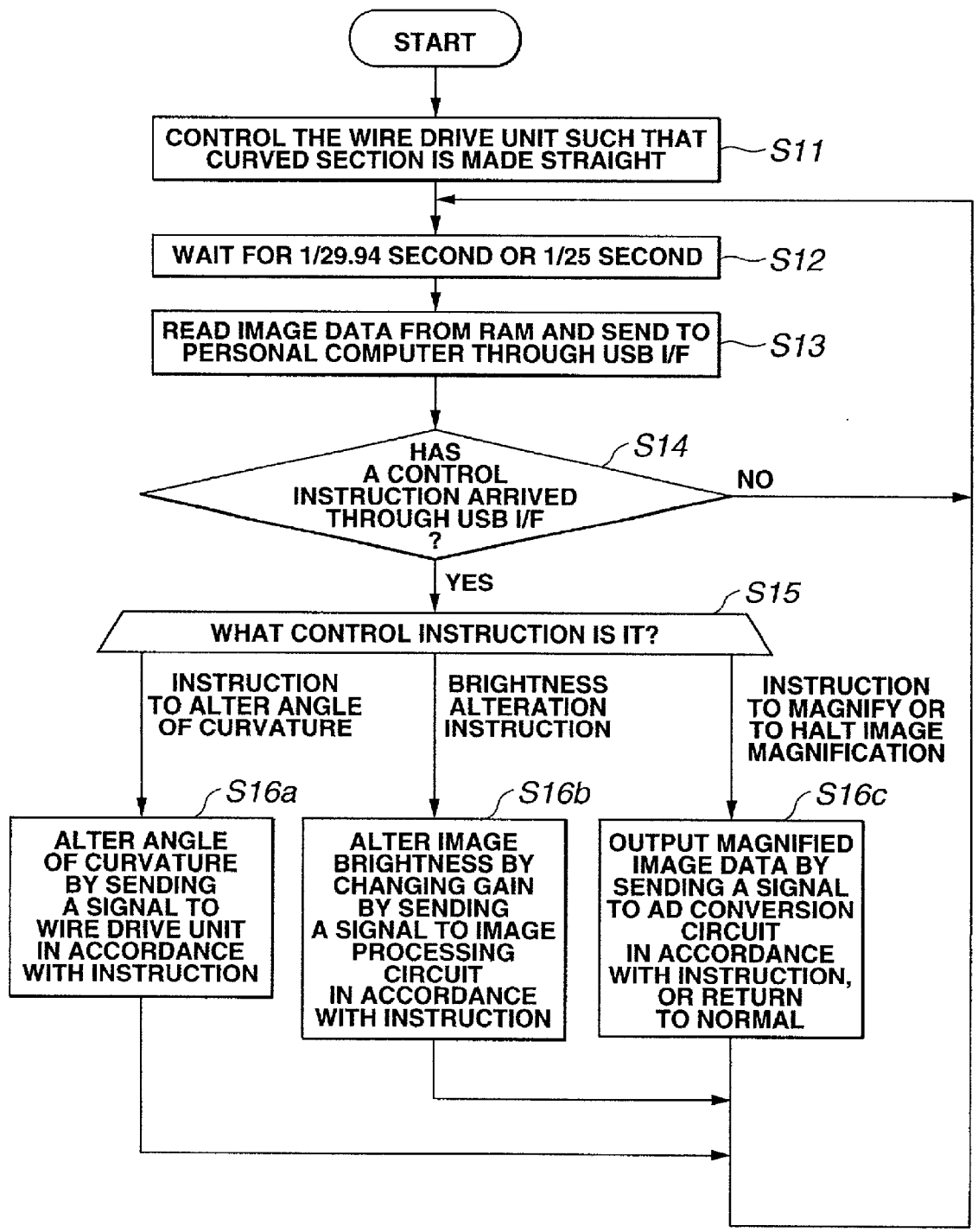
FIG. 6 is a flow chart illustrating the processing procedure of an endoscope according to the embodiment of the present invention.

FIG. 1 to FIG. 6 are views given for explanation of an embodiment of the present invention. FIG. 1 is a view showing the overall configuration of an endoscope system according to an embodiment of the present invention. FIG. 2 is a block diagram illustrating the internal configuration of a signal processing unit according to the embodiment of the present invention. FIG. 3 is a block diagram illustrating the configuration of a personal computer according to the embodiment of the present invention. FIG. 4 is a view illustrating an example of the configuration of a display screen on a monitor section of a liquid crystal display device (hereinbelow abbreviated to LCD) of a personal computer according to the embodiment of the present invention. FIG. 5 is a flow chart illustrating the processing procedure of a personal computer according to the embodiment of the present invention. FIG. 6 is a flow chart illustrating the processing procedure of an endoscope according to the embodiment of the present invention.

The endoscope system 1 according to the embodiment illustrated in FIG. 1 comprises an endoscope 2 whereby endoscopic examination is performed and a terminal device such as for example a notebook-type personal computer 3 connected to this endoscope 2, provided with the function of display means of an image captured by endoscope 2 and that performs centralized control of endoscope 2. The endoscope 2 and the personal computer 3 are connected solely by a single universal serial bus cable (hereinbelow abbreviated as USB cable) 4 constituting a serial communication cable for transferring image data captured by the endoscope 2 to the personal computer 3 and for transferring instructions from the computer 3 to the endoscope 2.

Rather than being of a special construction specific to this embodiment, the personal computer 3 is an ordinary personal computer such as is widely available commercially.

The endoscope 2 comprises an elongate insertion section 6 that is inserted in the direction of the part to be examined and a control section 7 provided at the proximal end of this insertion section 6.

The insertion section 6 comprises a hard tip section 8 provided at its tip, a curved section 9 that can be freely bent provided to the proximal end of this tip section 8, and a flexible section 10 having flexibility connected to the control section 7 from the proximal end of this curved section 9.

A light guide 11 whereby illuminating light is transferred is inserted into insertion section 6, the proximal end of light guide 11 being connected to a light source section 12 provided within control section 7. The light source section 12 has a lamp in its interior, the light generated by this lamp being incident on the end face of light guide 11 and transferred to the tip-side end face by means of this light guide 11.

The tip of the light guide 11 is mounted on an illuminating window of the tip section 8 so that the subject of image pick-up is an illuminated by this light being emitted forwards from the tip face and further passing through an illuminating lens 13. An observation window is provided adjacent to this illuminating window and the subject image is formed by an objective lens 14 mounted in the observation window. For example a CCD (charge coupled device) 15 constituting an image pick-up element is arranged at this position of image formation and photoelectric conversion is effected by this CCD 15.

This CCD 15 is connected to a signal processing unit 16 provided within the control section 7 by means of a signal line inserted into the insertion section 6. The CCD 15 is driven by this signal processing unit 16 and a video signal is generated by performing signal processing on its output signal. Also, the video signal is compressed to be converted to a signal capable and be transferred by the USB cable 4 constituting communication means having a transmission and receiving function.

The output signal of the signal processing unit 16 is transferred to the personal computer 3 through the USB cable 4. The USB cable 4 is provided at one end with a USB connector 18a connected to a USB connector socket 17 and at its other end is provided with a USB connector 18b connected to the personal computer 3.

The personal computer 3 returns the signal that is input by the USB connector 18b to the original video signal by performing signal processing and displays the image captured by the CCD 15 on the screen of an LCD monitor section 21 constituting a display device. This LCD monitor section 21, as will be described with reference to FIG. 4, is an image display section that performs centralized display of buttons etc. for implementing functions etc. for displaying the image captured by the endoscope 2 and for remote control of the bending operation etc. of the endoscope 2.

This personal computer 3 comprises a keyboard section 22 that performs data input etc., a mouse 23 constituting a pointing device for performing designation operations of various types and the LCD monitor section 21 that performs display of images etc. Its internal structure will be described later with reference to FIG. 3.

Also, a wire 24 for the bending curved section 9 is inserted within the insertion section 6 of the endoscope 2, the proximal end of the wire 24 being connected to a wire drive unit 25 within the control section 7. In addition, as will be described, it is arranged to be possible to bend the curved section 9 in any desired direction vertically or horizontally so that it can be inserted into a bent portion, or to effect observation etc. towards the direction of observation of the tip section 8 in a desired direction, by using the mouse 23 to perform an operation of selecting and designating a "bend" button displayed on the LCD monitor section 21 to drive a motor etc. in the interior of the wire drive unit 25 so as to pull on the wire 24.

FIG. 2 shows the internal configuration of the signal processing unit 7.

A drive circuit 31 generates a signal for driving the CCD and a timing signal that is supplied to a video processing circuit 32. In response to application of the drive signal from the drive circuit 31, the CCD 15 outputs a cumulative signal obtained by photoelectric conversion and this output signal is input to the video processing circuit 32.

The video processing circuit 32 performs video processing on the captured signal that is sent from the CCD 15 to convert it to a video signal by amplification and color separation etc. and outputs the result to an AD conversion circuit 33; it is also capable of changing the brightness of the image by altering the gain. Alteration of the image brightness is performed in accordance with a control signal output from CPU (Central Processing Unit) 34.

The AD conversion circuit 33 converts the output signal of the video processing circuit 32, which is an analogue signal, into digital image data. Under the control of an instruction from the CPU 34, the AD conversion circuit 33 is capable of performing AD conversion of the output signal of the video processing circuit 32 over the entire period under the control of an instruction from the CPU 34, or of AD conversion of the signal of only part of the period of the output signal. In the latter case, only a partial region of the video captured by the CCD 15 is magnified and converted to image data.

The image data that is output by the AD conversion circuit 33 is input to a compression processing circuit 35; this compression processing circuit 35 compresses the image data using a compression method suited to the input image data. The compressed image data is written to storage means constituted by RAM 36, i.e., it is stored. An RAM (Random Access Memory) 36 is controlled by the CPU 34 so that image data written to this RAM 36 can be read by the CPU 34.

The CPU 34 sequentially sends the image data to a USB interface (abbreviated as USB I/F in FIG. 2 etc.) 37. The CPU 34 is operated by a program stored in a ROM (read-only memory) 38.

The image data is converted to a USB standard signal by the USB interface 37. The USB interface 37 is connected to the USB connector socket section 17 and sends image data to the personal computer 3 through the USB cable 4 whose USB connector 18a is connected to this USB connector socket section 17.

The above operation is repeated at the frame period of the television, i.e., every 1/30 second (in the case of an NTSC system) or every 1/25 second (in the case of a PAL system). The signal processing unit 16 is of very small size since it is constituted entirely of semiconductors. Consequently, the control section 7 of the endoscope 2 of FIG. 1 is of small size and requires no manual control means of any sort, so it can be placed in any desired location inaccessible by human hands.

FIG. 3 shows the internal configuration of the personal computer 3. This configuration is that of an ordinary personal computer such as has become widely available commercially in recent years and is not specific to this embodiment. Therein, for a USB interface 45 and USB connector socket section 44, practically any type of device used in personal computers marketed in recent years may be provided.

A CPU 41 that performs overall control of the personal computer 3 is connected to an internal bus 42. RAM 43 that is utilized as the working area etc. of the CPU 41, the USB interface 45 that is connected to the USB connector socket section 44 and the connector of mouse 23 are connected to this internal bus 42; a mouse interface 46 is connected to this internal bus 42 through the connector socket section.

In addition, the keyboard section 22, a hard disk (abbreviated to HD in the figures) drive 47, a flexible disk (abbreviated as FD) drive 48 for a floppy disk etc. and a CD-ROM drive 49 are connected to this internal bus 42 by means of respective interfaces 22a, 47a, 48a and 49a.

Also, the LCD monitor section 21 is connected to the internal bus 42 and a RAM 43 through a display control circuit 50 that performs display control.

The CPU 41 first of all reads a program stored on the hard disk drive 47 and writes this to a prescribed region in the RAM 43 after which it operates in accordance with this program. The program is constructed so as to display a prescribed screen on the LCD monitor section 21 of the personal computer 3.

The data for display on the screen is prepared by the CPU 41 in a prescribed region in the RAM 43. The display control circuit 50 repeatedly reads the data for display on the screen and continually converts it into a signal for display on the LCD monitor section 21. This signal is sent to the LCD monitor section 21, where it is displayed as the monitor screen.

The screen data sent to the personal computer 3 from the endoscope 2 is received by the USB interface 45 and read by the CPU 41 through the internal bus 42. The CPU 41 uses a program to restore this image data to the image data prior to compression before writing it to a prescribed region of the RAM 43 so that it can be displayed on the LCD monitor section 21. This operation is performed repeatedly every 1/30 second (more precisely, every 1/29.94 second) or every 1/25 second, i.e., the television frame period.

The endoscope system in this embodiment is so constructed that the endoscope 2 and the personal computer 3 are connected using the USB cable 4 so that the endoscope 2 is controlled by control instructions transferred from the personal computer 3 through the USB cable 4 and image data of the image captured by the endoscope 2 is transferred to the personal computer 3 through the USB cable 4 so that the image can be displayed on the LCD monitor section 21. By adopting such a construction, implementation at low cost can be achieved, as a special-purpose centralized control device is not required, since only a personal computer 3 such as is widely available commercially is employed as the centralized control device.

Also, since a personal computer 3 of the notebook type can be employed as the centralized control device, it can be conveniently moved, being of small size and light weight.

Since only a personal computer 3 such as is widely available commercially is employed as the centralized control device, even if this breaks down, endoscopic examination can still be performed by substituting various other personal computers.

Also, since the centralized control device itself consists of the personal computer 3, saving of the observation images produced by the endoscope 2 can be achieved without needing to prepare another computer for purposes of saving these and the task of handing over the images to the other computer is also made unnecessary.

FIG. 4 illustrates the configuration of the monitor screen 51 displayed on the LCD monitor section 21.

Image data captured by the CCD 15 of the endoscope 2 is displayed in the central portion of a live image window 52 constituting an image display region. Specifically, the live image window 52 is a portion in which an observation image obtained by the endoscope 2 is displayed in the same way as with an ordinary television monitor.

Various buttons are displayed on a remote function panel section 53 in the monitor screen 51 constituting a display region for control purposes. The corresponding function is executed by clicking these buttons using the mouse 23 shown in FIG. 1.

Specifically, the U, D, L, and R buttons constituting curvature buttons 53a are buttons for remotely producing bending upwards, downwards, leftwards or rightwards from the current direction of curved section 9 of the endoscope, respectively, and a central button C is a button for putting the curved section 9 into the centered position, i.e., the straightforward direction.

For example, when the mouse 23 is used to click the U button, this control operation is transmitted to the CPU 41 through a mouse interface 46 etc. shown in FIG. 3; the CPU 41 thereby recognizes that the U button has been pressed. The CPU 41 then issues to the curved section 9 an instruction to bend upwards by a fixed angle from the current position. This instruction is transmitted to the endoscope 2 through the USB interface 45 and USB cable 4.

The signal processing unit 16 of the endoscope 2 shown in FIG. 2 transmits the aforesaid instruction to the CPU 34 through this USB interface 37. The CPU 34 decodes this instruction and sends to the wire drive unit 25 a signal for directing the angle of curvature upwards by a fixed amount compared with the current angle. The wire drive unit 25 rotates a built-in motor in accordance with this signal so that the wire 24 for producing upwards bending is wound up by a fixed amount. Thus, the curved section 9 is bent in the upward direction.

Also when the D, L and R buttons shown in FIG. 4 are clicked with the mouse 23, the angle of curvature of the endoscope 2 is changed in the desired direction by an identical action. Also when the C button is pressed, control of the wire drive unit 25 is performed such that all of the wires 24 for producing bending in the various directions are pulled or relaxed so as to effect return to the initial position. The curved section 9 of the endoscope 2 is thereby made to face in a straight forwards direction.

When a BRIGHT button 53b of FIG. 4 is clicked with the mouse 23, an instruction to make the image brighter is transmitted to the CPU 34 of the signal processing unit 16 of FIG. 2 by the same path as described above. The CPU 34 decodes this signal and sends a signal for making the gain larger than the current condition to the video processing circuit 32. In response to this, the video processing circuit 32 increases the gain, so that a video signal from the CCD 15 is output after being amplified with a larger gain. The brightness of the live image that is displayed in the live image window 52 at FIG. 4 is thereby increased. Contrariwise, if a DARK button 53c is clicked, the brightness of the live image is reduced.

Also, if a TELE button 53d is clicked, an instruction to magnify the image is sent to the endoscope 2 from the personal computer 3. The CPU 34 of signal processing unit 16 of FIG. 2 decodes this instruction and sends a signal for effecting AD conversion and producing output to the AD conversion circuit 33 only during a part of the period of the output signal of the video processing circuit 32. In response to this, the AD conversion circuit 33 outputs digital image data consisting of a signal of only part of the period of the video signal captured by the CCD 15, magnifying the digital image data to correspond to the whole. Thus, the image displayed in the live image window 52 of FIG. 4 is an image obtained by magnifying, to correspond to the whole, only part of the video captured by the CCD 15. Clicking the WIDE button 53e provokes return to the original size, causing the entire video captured by the CCD 15 to be displayed as the image. The mode of display of the image displayed in the window 52 can thus be controlled by pressing the buttons 53b to 53e.

A STORE button 53f of FIG. 4 is a button for saving the image displayed in the current live image window 52, i.e., the image that is currently being observed by the endoscope 2 in memory constituted of a hard disk, by means of a hard disk drive 47 in personal computer 3.

When this STORE button 53f is clicked, the CPU 41 of personal computer 3 of FIG. 3 gives instructions for the image data arranged in the RAM 43 for display to be copied to another region within the RAM 43. The CPU 41 then controls a hard disk interface 47a so as to write this image data in the RAM 43, which has thus been copied, to a hard disk drive 47 as a file.

When the hard disk interface 47a receives this instruction, it writes the image data in the RAM 43 to the hard disk drive 47 as a file. After this, the CPU 41 reads and compresses the image data placed in the RAM 43 and writes this to a thumbnail region that is secured within the RAM 43.

This thumbnail region in the RAM 43 is constantly read by the display control circuit 50 of FIG. 3 and is displayed as a thumbnail images 54a in a thumbnail window 54 on the monitor screen 51 of FIG. 4. A compressed image of a large number of images that have previously been saved on the hard disk drive 47 are displayed as the thumbnail images 54a in the thumbnail window 54.

When a VIEW button 55a of a general function panel 55 of FIG. 4 is clicked, an image in the hard disk drive 47 corresponding to the thumbnail image 54a selected beforehand by being clicked by the mouse 23 is read and placed in the RAM 43. The CPU 41 instructs the display control circuit 50 to display the image that has been written to the RAM 43.

This image that has been read from the hard disk drive 47 is therefore displayed in the live image window 52 instead of the current endoscope observation image input from the USB interface 45. If the VIEW button 55a is again clicked, the CPU 41 stops this display and returns to the operation of displaying the current endoscope observation image that is input from the USB interface 45 as before.

An EXPORT button 55b is a button that is employed when it is desired that the image on the hard disk drive 47 corresponding to the thumbnail image 54a that was clicked is written to a flexible disc constituting a portable recording medium inserted into flexible disc drive 48. An EXIT button 55c is a button that is clicked to stop the program of personal computer 3 and terminate use of the endoscope system 1.

The instructions that are sent to the endoscope 2 from the personal computer 3 through the USB cable 4, such as instructions for alteration of the angle of curvature described above, are transmitted in an extremely short time, so they are transmitted in the intervals of the image data transmission described above performed from the endoscope 2 in respect of the personal computer 3 with the frame period of the television.

FIG. 5 is a flow chart of the processing performed at the personal computer side of this endoscope system 1 whereby the above operation can be performed. FIG. 6 is a flow chart of the processing performed by the CPU 41 in the control section 7 of the endoscope 2 of this endoscope system 1 whereby the above operation can be performed. The description will commence from FIG. 5.

When the power source of the personal computer 3 is turned on, as shown in step S1, the CPU 41 reads the program from the hard disk drive 47 and stores it in the RAM 43.

Next, in accordance with this program, the CPU 41 displays all of the images saved on the hard disk drive 47 as the thumbnail images 54a in the thumbnail window 54.

Next, in step S3, the CPU 41 ascertains whether or not image data has arrived at the USB interface 45 from the endoscope 2. If no images have in fact arrived, processing then shifts to step S5. On the other hand, if an image has arrived, processing advances to the next step S4 in which restoration processing is performed on the incoming image data to reconstitute the endoscope image prior to compression; processing then advances to step S5 in which this endoscope image is displayed in the live image window 52.

In step S5, the CPU 41 ascertains whether or not a button has been clicked by the mouse 23; if it is ascertained that no button has been clicked, processing returns to step S3; if a button has been clicked, processing advances to step S6 in which it is further ascertained which button has been clicked.

If an EXIT button 55c is clicked, processing is terminated.

Also, as shown in step S7a, if any of the curvature buttons 53a (specifically, the U, D, L, R, or C button), the BRIGHT button 53b, the DARK button 53c, the TELE button 53d, or the WIDE button 53e has been clicked, the corresponding instruction is sent to the endoscope 2 through the USB interface 45, after which processing returns to step S3.

On the side of the endoscope 2, the CPU 34 decodes the incoming instructions and exercises control such that the corresponding action is performed in accordance with this decoding.

Also, if the STORE button 53f is clicked as shown in step S7b, the image displayed in the live image window 52 is saved on the hard disk drive 47, after which processing shifts to step S8b, in which thumbnail image data of the saved image is generated and the thumbnail image 54a is added to the thumbnail window 54; processing then returns to step 3.

Also, as shown in step S7c, if the VIEW button 55a is clicked, an image corresponding to the thumbnail image that was clicked beforehand is read from the hard disk drive 47 and displayed in the live image window 52; processing then returns to step 3 after waiting for the VIEW button 55a to be clicked again as shown in step S8c.

Also, when the EXPORT button 55b is clicked as shown in step S7d, an image corresponding to the thumbnail image that was previously clicked is read from the hard disk drive 47, output to the floppy disk drive 48 and written to the floppy disk, after which processing returns to step 3.

Next, the processing on the side of the endoscope 2 will be described referring to FIG. 6.

When the power source on the endoscope 2 is turned on, the CPU 34 is operated in accordance with the program 38 stored in the ROM 38 and, in initial step S11, controls the wire drive unit 25 such that curved section 9 becomes straight.

Next, the CPU 34 waits for the lapse of 1/29.94 second (or 1/25 second) (step S12); the CPU 34 then reads the image data temporarily stored in the RAM 36 and transmits this (step S13) to the personal computer 3 through the USB interface 37.

After transmission of the image data, in the following step S14, this CPU 34 ascertains whether or not a control instruction has arrived through the USB interface 37; if no control instruction has arrived, it returns to step S12.

On the other hand, if a control instruction has arrived, the CPU 34 ascertains the identity of the control instruction (step S15).

If it then identifies an instruction to alter the angle of curvature, the CPU 34, as shown in step S16a, sends a signal in accordance with this instruction to the wire drive unit 25 to perform alteration of the angle of curvature; after this, it returns to step S12.

Also, if it then identifies an instruction to alter the brightness, the CPU 34, as shown in step S16b, sends a signal in accordance with this instruction to the video processing circuit 32 to alter the brightness of the image by altering the gain, after which it returns to step S12.

Also, if it is identified as an instruction to magnify or to stop magnification of the image, the CPU 34, as shown in step S16c, sends a signal in accordance with this instruction to the AD conversion circuit 33 to output image data wherein the image has been magnified or to perform control to return to normal, after which it returns to step S12.

This embodiment has the following benefits.

The endoscope 2 can be operated remotely. Also, since only a personal computer 3 such as is widely available commercially is employed as the device for operating the endoscope 2, the endoscope system 1 can be constructed with low cost.

Also, since a notebook-type personal computer 3 can be employed as the device for operating the endoscope 2, this can be conveniently moved about in view of its small size and light weight. Also, since only a personal computer 3 such as is widely available commercially is employed as the device for operating the endoscope 2, even if this breaks down, endoscopic examination can still be performed by substituting various other personal computers.

Also, since the device itself for operating the endoscope 2 is constituted by a personal computer 3, there is no need to provide another computer for saving the images and saving of images can be achieved without an operation to hand over the images.

Also, since the endoscope 2 and the personal computer 3 can be connected using only a single USB cable, the tasks of installation, moving or dismantling the endoscope system 1 are facilitated. Also, since no manual control means at all need be arranged on the control section 7 of the endoscope 2, the control section 7 can be made of small size, light weight and low cost and the degree of freedom regarding its location of installation can be increased.

Although, in the above description, the case was described in which manual control of the various functions were performed using the mouse 23, an identical control operation could be performed by allocating keys of the keyboard section 22 of the personal computer 3 to these respective functions and pressing these keys instead of using the mouse 23.

It should be noted that the personal computer 3 used to construct the endoscope system 1 by connection to the endoscope 2 by means of the USB cable 4 is not restricted to existing operating systems such as for example Microsoft Windows (R) 98 or 2000 etc. or Linux etc.

Also, the endoscope system 1 could be constituted by connecting a personal computer 3 operated by such an existing operating system, to the endoscope 2 by means of the USB cable 4.

In this case, operation as described above is performed by using a CD-ROM or flexible disk etc. to install a device driver enabling the personal computer 3 to recognize the endoscope 2 and/or an application program whereby the various types of centralized control described above are made possible on the personal computer 3. That is, an endoscope system 1 can be constructed whereby centralized control of the endoscope 2 is performed by the personal computer 3.

Thus, if this is done, even if the personal computer 3 used to construct the endoscope system 1 breaks down, a substitute endoscope system 1 can be constructed in a straightforward manner by installing the application program etc. on another personal computer 3.

Also, if this is done, the personal computer 3 may be moved together with the endoscope 2 to the location where the endoscope 2 is employed; however, even without moving the personal computer 3, the endoscope system 1 could be constructed utilizing a personal computer 3 at the moved destination.

Also, expansion of functions etc. can be achieved by arranging for alteration of the program on the endoscope 2 to be performed in a simple fashion from the personal computer 3 by constructing the ROM 38 on the endoscope 2 shown in FIG. 2 by rewritable non-volatile semiconductor memory such as, for example, specifically, an EEPROM or flash memory.

Also, by connecting a personal computer 3 operated by an existing operating system with the endoscope 2 by means of the USB cable 4, an endoscope system 1 in respect of an ordinary personal computer 3 can be constructed in a straightforward fashion by arranging to transfer the device driver and/or application software whereby the endoscope 2 is recognized and control of the endoscope 2 is made possible to personal computer 3 from the endoscope 2.

For this purpose, a data recording device recognized through the USB cable 4 in an existing operating system employed in a personal computer 3 may be provided at the endoscope 2 and the aforesaid device driver and/or application software programs may be stored on this data recording device.

As described above, according to this embodiment of the invention, an endoscope system comprises an endoscope and an image display section that displays the image of a subject captured by an image pick-up element provided in the endoscope. The endoscope comprises a connector that is detachably connected to a serial communication cable and a signal processing circuit that converts an image captured by the image pick-up element to a signal capable of being transmitted via the serial communication cable. The image display section is a screen displayed on a display device of a terminal device connected to the serial communication cable; the screen comprises an image display region utilized for display of the image captured by the image pick-up element and a display region for control purposes whereby control of the endoscope is performed. Consequently, the display section of the personal computer can be utilized for displaying the image without needing special-purpose image display means and the personal computer can be employed as control means that performs control of the endoscope, without requiring a special-purpose control device; thus an endoscope system can be constituted with low cost. Also, the location where endoscopic examination is performed can easily be changed.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:
1. An endoscope system comprising:
an endoscope; and
an image display section that displays the image of a subject captured by an image pick-up element provided in this endoscope,
wherein said endoscope comprises:
a connector for connecting a serial communication cable detachably; and
a signal processing circuit that converts the image captured by said image pick-up element to a signal capable of being transmitted via said serial communication cable; and wherein said image display section is a screen displayed on the display section of a terminal device connected to said serial communication cable; and said screen comprises an image display region used for display of an image captured by said image pick-up element and a display region for directional motion control purposes whereby directional motion control of said endoscope is performed.

2. The endoscope system according to claim 1 wherein said terminal device is a personal computer.

3. The endoscope system according to claim 1 wherein said endoscope comprises a curved section that can be freely bent, and said display region for directional motion control purposes comprises a function of bending said curved section remotely.

4. The endoscope system according to claim 1 wherein said display region for control purposes is capable of controlling the mode of display of the image captured by said image pick-up element that is displayed on said display section of said terminal device.

5. The endoscope system according to claim 1 wherein said display region for control purposes comprises a function of storing in memory the image data captured by said image pick-up element that is displayed in said display section of said terminal device.

6. The endoscope system according to claim 5 wherein said display region for control purposes further comprises a function of recording on to a portable recording medium the image data stored in said memory.

7. An endoscope system comprising an endoscope having an insertion section and image display means that displays a subject image captured by image pick-up means provided in this endoscope, comprising:
  a connector for connecting a serial communication cable detachably to said endoscope;
  signal processing means provided in said endoscope and that converts the image captured by said image pick-up means into a signal capable of being transmitted via said serial communication cable; and
  a personal computer connected via said serial communication cable;
  wherein a display portion of said personal computer is arranged to be used as centralized directional motion control means of the endoscope, including display of the image captured by said image pick-up means.

8. The endoscope system according to claim 7 wherein said endoscope comprises a curved section that can be freely bent, and said centralized directional motion control means is capable of remotely bending said curved section.

9. The endoscope system according to claim 7 wherein said centralized control means is capable of controlling the display mode of the image captured by said image pick-up means that is displayed on the display section of said personal computer.

10. The endoscope system according to claim 7 wherein, on the display section of said personal computer, in addition to the display of the image captured by said image pick-up means, a plurality of functions are displayed and said centralized control means performs control such as to execute the function designated by selection designation means.

11. The endoscope system according to claim 10 wherein the functions designated by said selection designation means include a function of storing in memory image data captured by said image pick-up means displayed on said display section of said personal computer.

12. The endoscope system according to claim 11 wherein the functions designated by said selection designation means further comprise a function of recording on a portable recording medium image data stored in said memory.

13. The endoscope system according to claim 7 wherein said personal computer is operated with a prescribed operating system and said personal computer is capable of centralized control of said endoscope by installing on said personal computer a software program for making it possible to control said endoscope.

14. An endoscope device comprising:
  image pick-up means that captures the image of a subject;
  image processing means that generates a video signal by video signal processing for an image pick-up signal output from said image pick-up means;
  compression processing means that generates image data by compressing the video signal from said video processing means;
  storage means that stores image data generated by said compression processing means;
  reading control means that controls reading of said storage means;
  transmission means for outputting image data read from said storage means;
  reception means that receives control information for controlling the function of said video processing means said control information being input via a controlling video unit controlling the direction of motion of the endoscope portion of a display of a central controller;
  video processing control means that controls said video processing means in accordance with the control information received by said reception means; and
  communication control means that controls said transmission means and said reception means.

15. The endoscope device according to claim 14 wherein said transmission means and said reception means perform transmission of said image data and reception of said control information respectively via a serial communication cable.

16. An endoscope system comprising an endoscope having an insertion section and image display means for displaying a subject image captured by image pick-up means provided in this endoscope; said endoscope system further comprising:
  a connector for connecting a serial communication cable detachably to said endoscope; and
  a personal computer connected via said serial communication cable;
  wherein the display section of said personal computer is employed as display means used for display of an image captured by said image pick-up means and said display section of the personal computer is used for directional motion control means that performs directional motion control of the endoscope.

17. The endoscope system according to claim 16 wherein said endoscope comprises a freely bendable curved section and said control means comprises a function of bending said curved section remotely.

18. The endoscope system according to claim 16 wherein said control means is capable of controlling the display mode of the image captured by said image pick-up element displayed in the display section of said personal computer.

19. The endoscope system according to claim 16 wherein said control means comprises a function of storing in memory image data captured by said image pick-up means displayed in the display section of said personal computer.

20. The endoscope system according to claim 19 wherein said control means further comprises a function of recording image data stored in said memory on to a portable recording medium.

* * * * *